US00PP17521P2

(12) United States Plant Patent
Pellett

(10) Patent No.: US PP17,521 P2
(45) Date of Patent: Mar. 27, 2007

(54) MINIATURE ROSE PLANT NAMED 'KOROSKIN'

(50) Latin Name: *Rosa hybrida*
Varietal Denomination: KORoskin

(75) Inventor: Gary R. Pellett, Central Point, OR (US)

(73) Assignee: W. Kordes' Söhne Rosenschulan GmbH & Co KG, Offenseth-Sparrieshoop (DE)

( * ) Notice: Subject to any disclaimer, the term of this patent is extended or adjusted under 35 U.S.C. 154(b) by 72 days.

(21) Appl. No.: 11/255,016

(22) Filed: Oct. 19, 2005

(51) Int. Cl.
*A01H 5/00* (2006.01)

(52) U.S. Cl. ..... Plt./116

(58) Field of Classification Search ..... Plt./116, Plt./119
See application file for complete search history.

(56) References Cited

PUBLICATIONS

Canada 04–4490 Dec. 1, 2004 W. Kordes' Söhne.

*Primary Examiner*—Kent Bell
*Assistant Examiner*—June Hwu

(57) ABSTRACT

A new and distinct variety of miniature rose with long lasting, novel golden bronze flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from axsexual propagation.

1 Drawing Sheet

Genus, species and variety denomination: The botanical classification of the new rose plant is *Rosa hybrida* 'KORoskin'.

BACKGROUND OF THE INVENTION

The present discovery constitutes a new and distinct variety of a miniature pot rose plant which was discovered in a cultivated area in July, 2003. The new rose variety resulted from a naturally occurring mutation of unknown causation on a branch of 'KORstoffein', a patented rose described and illustrated in U.S. Plant Pat. No. 11,242 issued on Feb. 22, 2000.

The new rose plant was asexually propagated for further evaluation. This new and distinctive miniature rose variety is named 'KORoskin'.

SUMMARY OF THE DISCOVERY

The new rose plant may be distinguished from 'KORstoffein', by the following combination of characteristics:

1. The general tonality of the flower of 'KORoskin' is Yellow-Orange Group 23C while the general tonality of the flower of 'KORstoffein' is Yellow-Orange Group 19D;
2. Flowers last longer on the plant of the mutation; and
3. The foliage of the parent variety has a glossy texture while the foliage of 'KORoskin' has a matte finish.

The new and distinct rose plant was selected due to its':

1. Compact and uniform growth and flowering under greenhouse conditions when grown as a potted floral plant;
2. Abundant, long lasting, and attractive golden bronze flowers on upright stems;

3. Resistance to diseases encountered in greenhouse culture; and
4. Suitability for production from softwood cuttings in floral and nursery containers;

This combination of qualities is not present in prior rose cultivars. These objectives have been substantially achieved and in that distinguish 'KORoskin' from all other varieties of which I am aware.

As part of the rose development program, Gary Pellett asexually propagated the mutation by rooting cuttings and conducted evaluations and observations on the resulting plants in a controlled environment in Jackson County, Oreg. The resulting seedlings exhibited distinctive physical and biological characteristics. The first asexual reproduction of 'KORoskin' was done by rooting softwood cuttings in July, 2003 at the Newflora LLC Nursery in Central Point, Oreg.

This initial and other subsequent propagations conducted in controlled environments show that the foregoing and all other characteristics of 'KORoskin' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORoskin'. Specifically illustrated in SHEET ONE:

A flowering stem;

A tight bud and partially opened flower blooms;

Flower petals, detached;

Dissected receptacle and detached sepals;

A portion of a stem exhibiting thorns; and

Two leaves.

DETAILED BOTANICAL DESCRIPTION

The following is a description of 'KORoskin', as observed in its growth in September, 2005 in a nursery in Jackson County, Oreg. on plants of two years of age. Color references are made using The Royal Horticultural Society (London, England) Colour Chart, 2001 except where common terms of color are used.

For a comparison, several physical characteristics of the rose variety 'KORstoffein' are compared to 'KORoskin' in Chart 1.

CHART 1

| Characteristic: | 'KORoskin' | 'KORstoffein' |
|---|---|---|
| General tonality of open blooms. | A blend of Yellow-Orange Group 22C and Greyed-Red Group 181D. | Yellow-Orange Group 19D. |
| Leaf finish. | Matte. | Glossy. |

For comparison to most similar variety is 'KORspunty' (U.S. Plant patent application Ser. No. 11/155,408). 'KORspunty' has glossy leaves, strong foliaceous appendages, and fewer, smaller prickles while 'KORoskin' has matte leaves, weak foliaceous appendages and larger prickles.

Parent:

*Parent.*—Spontanious mutation of 'KORstoffein' U.S. Plant Pat. No. 11,242 issued on Feb. 22, 2000.

Classification:

*Botanical classification.*—*Rosa hybrida,* var. 'KORoskin'.

*Commercial classification.*—Miniature.

FLOWER AND FLOWER BUD

Blooming habit: Continuous.

Flower bud:

*Size.*—Upon opening, 25 mm in length from base of receptacle to end of bud.

*Bud form.*—Long, pointed ovoid.

*Bud color.*—As sepals first unfold, bud color is a blend of Greyed-Red Group 180B and Orange-Red Group N34C. When ¼ open, the bud is a blend of Orange-Red Group N34d and Orange-Red Group 35D.

*Sepals.*—Size: Average 25 mm long×7–8 mm wide. Shape: Foliaceous appendages are weak or lacking. Sepal apex is cirrose. Base is flat at union with receptacle. Quantity: Five. Surface texture: Surface of sepals is moderate to strongly pubescent. Limited numbers of stipitate glands are present. Color: Upper surface Green Group 138A. Lower surface Green Group 138A. Intonations present of Greyed-Red Group 182B on upper and lower sepal surfaces.

*Receptacle.*—Surface: Smooth. Color: Green Group 138A with intonations of Greyed-Red Group 182B. Shape: Broadly funnel shaped. Size: 6–8 mm (h)× 5–6 mm (w).

*Peduncle.*—Surface: With limited numbers of stipitate glands. Length: 30–40 mm average length. Diameter: 2 mm average diameter. Color: Green Group 137D. Intonations of Greyed-Red Group 182B. Strength: Upright and strong. Borne: Most often, singly.

Flower bloom:

*Fragrance.*—Little to no fragrance.

*Duration.*—Very long lasting. A blooming plant with flowers has a commercial shelf life of days. The blooms have a duration on the plant of approximately 15–20 days.

*Size.*—Medium. Average flower diameter is 40–50 mm when open.

*Form.*—Shape of flower when viewed from the side: Upon opening, upper part: Flattened convex to convex. Upon opening, lower part: Flattened convex to convex. Open flower, upper part: Flattened convex. Open flower, lower part: Flattened convex.

Color:

*Upon opening, petals.*—Outermost petals: Outer Side: Petal color is a blend of Red Group and Greyed-Red Group 180D. The upper margin is Greyed-Red Group 179D. Inner Side: Yellow-Orange Group 23C. Innermost petals: Outer Side: Petal color is a blend of Red Group and Greyed-Red Group 180D. The upper margin is Greyed-Red Group 179D. Inner Side: Yellow-Orange Group 23C.

*Upon opening, basal petal spots.*—Basal petal spot, outermost petals: Outer Side: Yellow Group 12D. Inner Side: Yellow Group 12D. Basal petal spot, innermost petals: Outer Side: Yellow Group 12C. Inner Side: Yellow Group 12C.

*After opening, petals.*—Outermost petals: Outer Side: Red Group 38B. Middle zone of petal Greyed-Red Group 180D. Upper margin of petal Red Group 38C. Inner Side: Yellow-Orange Group 20C. Innermost petals: Outer Side: Red Group 38B. Middle zone of petal Greyed-Red Group 180D. Upper margin of petal Red Group 38C. Inner Side: Yellow-Orange Group 16D.

*After opening, basal petal spots.*—Basal petal spot, outermost petals: Outer Side: Yellow Group 12D. Inner Side: Yellow Group 12D. Basal petal spot, innermost petals: Outer Side: Yellow Group 12D. Inner Side: Yellow Group 12D. Variegations: Many petals with a band of Green-Yellow Group 1D extending up from the basal zone into the middle zone of the petal. This band of color diminishes as the flower opens.

General tonality: On open flower, a blend of Yellow-Orange Group 22C and Greyed-Red Group 181D. No change in the general tonality at the end of the fifth day. Afterwards, general tonality is Yellow-Orange Group 22D and Green-Yellow Group 161D.

Petals:

*Petal count.*—Double. Approximately 25–30 petals under normal conditions.

*Petal reflex.*—Petals reflex slightly.

*Petal edge.*—Smooth. Many petals with a point in center of the upper margin.

*Petal shape.*—Round. Shape of base is deltoid.

*Petal size.*—18–20 mm long; 10–15 mm wide.

*Thickness.*—Average.

*Petal arrangement.*—Imbricated.

*Petaloids.*—Present. Average of 3–5 per flower. Petaloids are 8–10 mm long and 3–5 mm wide. Petaloids are a blend of Red Group 40C and Yellow-Orange Group 21C. Surface texture is smooth. Petaloids are varied in shape, linear to elliptic. Petaloids often contorted.

Reproductive organs:

*Pistils.*—Average. Approximately 40 present. Stigmas: Location: Mostly inferior in position to anthers. Color: Yellow-Green Group 148D. Styles: Length: 4–6 mm long. Color: Green-White Group 157A. Limited intonations on upper portion of styles of Greyed-Red Group 182B.

*Stamens.*—Approximately 40–45 on average and regularly arranged around the styles. Anthers: Size: 2 mm long. Color: Green-Yellow Group 160B and Greyed-Orange Group 163C. Pollen: Scant. Color: Green-Yellow Group 160A. Filaments: Color: Yellow-Green Group 151B. Length: 4–6 mm.

THE PLANT

Plant growth: Moderately vigorous. Upright to bushy habit. When grown as a 10.5 cm pot plant, the average height of the plant itself is 18–20 cm and the average width is 16–18 cm. When grown as a budded nursery plant the average plant height is 65–75 cm and the average plant width is 50 cm.

*Stems.*—Stem color: Young wood: Green Group 138A. Older wood: Green Group 138A. Stem surface: Young wood: Smooth. Older wood: Smooth.

*Prickles.*—Present. Incidence: 4–5 per 10 cm of stem. Size: Average length: 5 mm. Color: Green-White Group 157A. Intonations of Greyed-Red Group 182B present throughout the thorn. Shape: Linear to downward hooked.

*Leaves and leaflets.*—Normally 5 leaflets on normal leaves in middle of the stem. Leaf size: 90–100 mm (l)×50–55 mm (w). Quantity: Average abundance. Texture: Matte. Smooth. Color, mature foliage: Upper Leaf Surface: Green Group 137C. Lower Leaf Surface: Green Group 138C. Color, juvenile foliage: Upper Leaf Surface: Green Group 137C. Lower Leaf Surface: Green Group 138C. Anthocyanin intonation: Present on juvenile foliage. Location: Intonations of Greyed-Red Group 182B present on leaflet margins, petioles, and stipules.

*Stipules.*—Size: Main portion of stipules10–12 mm (l) — 4–5 mm (w). At the tips, the stipules are 8–10 mm across. Stipule color: Green Group Green Group 137C. Intonations of Greyed-Red Group 182B present on juvenile tissue, Presence of stipitate glands: Present on margins. Margins: Serrated.

*Petiole.*—Length: 20 mm average length. Diameter: 1.25 mm average diameter. Underneath: Smooth. A few small white hairs present. Petiole color: Green Group 138C. Intonations of Greyed-Red Group 182B present on margins of juvenile foliage. Prickles: None observed. Stipitate glands: A few.

*Petiole rachis.*—Color: Green Group 138A above and below. Anthocyanin: On margins. Color Greyed-Red Group 182B. Prickles: Generally absent. Stipitate glands: A few on margins.

*Leaflets.*—Size: Average size of the terminal leaflet is 90–100 mm (l) ×50–55 mm (w). Shape: Ovate. Margins: Finely serrated. Texture: Thin.

Hips/seed formation: None observed.

Winter hardiness: To date, the variety has been grown sucessfully in Zone 5.

Disease resistance: Above average resistance to powdery mildew and Botrytis under normal growing conditions.

I claim:

1. A new and distinct variety of miniature rose plant characterized by the following combination of characteristics:

(a) forms abundant, attactive long lasting golden bronze flowers;

(b) exhibits a compact and bushy growth habit;

(c) is suited for growing in greenhouse in pots from softwood cuttings, and;

(d) exhibits durable flowers and foliage suitable for distribution in the floral industry;

substantially as herein illustrated and described.

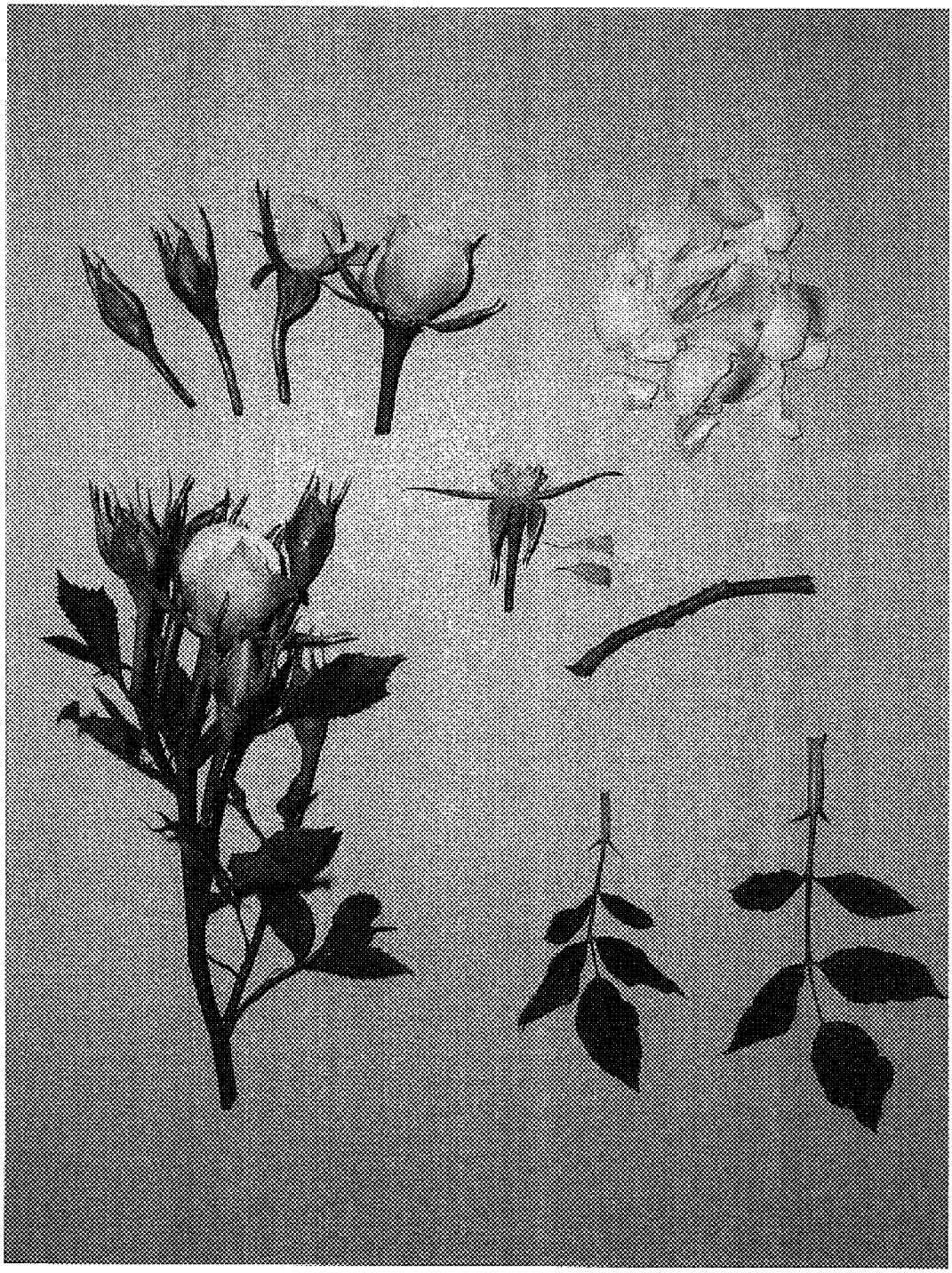

* * * * *